United States Patent
Svendsen

(10) Patent No.: US 6,667,290 B2
(45) Date of Patent: Dec. 23, 2003

(54) SUBSTRATE TREATED WITH A BINDER COMPRISING POSITIVE OR NEUTRAL IONS

(76) Inventor: Jeffrey S. Svendsen, P.O. Box 795754, Dallas, TX (US) 75379

( * ) Notice: Subject to any disclaimer, the term of this patent is extended or adjusted under 35 U.S.C. 154(b) by 28 days.

(21) Appl. No.: 10/217,294

(22) Filed: Aug. 12, 2002

(65) Prior Publication Data

US 2003/0054970 A1 Mar. 20, 2003

Related U.S. Application Data

(60) Provisional application No. 60/323,573, filed on Sep. 19, 2001.

(51) Int. Cl.$^7$ .................................................. C11D 1/62
(52) U.S. Cl. ....................... 510/438; 510/234; 510/237; 510/238; 510/245; 510/254; 510/363; 510/365; 510/382; 510/384; 510/391; 510/504
(58) Field of Search ................................. 510/234, 237, 510/238, 245, 254, 363, 365, 382, 384, 391, 504, 438

(56) References Cited

U.S. PATENT DOCUMENTS

| | | | |
|---|---|---|---|
| 3,283,357 A | 11/1966 | Decker et al. ................. | 15/506 |
| 4,012,353 A | 3/1977 | Chasin et al. ............... | 260/29.6 |
| 4,151,148 A | 4/1979 | Chasin et al. ............... | 260/29.6 |
| 4,540,505 A * | 9/1985 | Frazier ........................ | 252/106 |
| 4,946,617 A | 8/1990 | Sheridan et al. ............... | 252/91 |
| 4,987,632 A | 1/1991 | Rowe et al. ............. | 15/104.93 |
| 5,435,935 A * | 7/1995 | Kupneski ..................... | 252/156 |
| 5,856,290 A * | 1/1999 | van Buskirk et al. ........ | 510/382 |
| 5,962,001 A | 10/1999 | Rose et al. .................. | 424/404 |
| 5,965,514 A * | 10/1999 | Wierenga et al. ............ | 510/433 |
| 6,013,615 A * | 1/2000 | Zhou et al. .................. | 510/434 |
| 6,136,770 A * | 10/2000 | Cheung et al. .............. | 510/384 |

FOREIGN PATENT DOCUMENTS

WO       WO 02/48296 A2    6/2002

* cited by examiner

*Primary Examiner*—Charles Boyer
(74) *Attorney, Agent, or Firm*—Steven W. Smith

(57) ABSTRACT

An article for sanitizing a surface with a sanitizing solution while maintaining the concentration level of a sanitizer in the sanitizing solution at an effective concentration level. A substrate that absorbs and holds the sanitizing solution is treated with a sanitizer release polymer composition. The substrate may be a woven, nonwoven, or knit fabric, a foam or sponge, or the like. The sanitizer release polymer composition may include a cationic or nonionic surfactant or binder that is operable to maintain the concentration level of the sanitizer at the effective level during prolonged periods of use.

33 Claims, 1 Drawing Sheet

SUBSTRATE TREATED WITH A BINDER COMPRISING POSITIVE OR NEUTRAL IONS

PRIORITY STATEMENT UNDER 35 U.S.C. §119 (e) & 37 C.F.R. §1.78

This nonprovisional application claims priority based upon the prior U.S. provisional patent application entitled, "Enhanced Sanitizer Release Polymer Composition," application No. 60/323,573, filed Sep. 19, 2001 in the name of Jeffrey Scott Svendsen.

BACKGROUND OF THE INVENTION

1. Technical Field of the Invention

This invention relates to treated substrates containing sanitizer release polymer compositions and, more particularly, to a sanitizing towel treated with an enhanced sanitizer release polymer composition for releasing cationic sanitizers.

2. Description of Related Art

In order to control microbial growth on a surface, a sanitizing solution containing antimicrobials such as sanitizers is applied to the surface with a substrate such as a woven or nonwoven fabric. A sanitizer is a compound that reduces microbial contaminants to safe levels as determined by government Public Health requirements. Currently, the safe level is a 99.999% reduction in the bacterial count.

For the process to be effective, the sanitizing solution must maintain a certain concentration of sanitizer. A serious problem occurs when the woven or nonwoven fabric reduces the concentration of sanitizer in the sanitizing solution. For example, a nonwoven fabric is repeatedly rinsed in a sanitizing solution contained in a bucket, while sanitizing the tabletop surfaces of a restaurant. If the nonwoven fabric is diluting or reducing the effectiveness of the sanitizer in the sanitizing solution, then the tabletop surfaces are not being disinfected. This can lead to an outbreak of pathogenic enteric bacteria, such as nearly all members of the genus Salmonella or E. coli. Pathogenic enteric bacteria can cause illness, or worse death.

In the field of sanitizers, guidelines exist for the minimum concentration of sanitizer in a sanitizing solution to avoid outbreaks of pathogenic enteric bacteria. The two most common sanitizers in sanitizing solutions are quaternary ammonium compound (QAC)-based or chlorine-based sanitizers. For example, by law, QAC-based sanitizer sanitizing solutions must maintain a concentration level of 200–400 parts per million to achieve the 99.999% reduction in the bacterial count.

Structurally, QACs contain four carbon atoms linked directly to one nitrogen atom through covalent bonds and four alkyl groups. The portion attached to the nitrogen atom by an electrovalent bond may be any anion, but it is usually chloride or bromide to form the salt. The nitrogen atom with the attached alkyl groups forms the positively charged cation portion. Depending on the nature of the R groups, the anion and the number of quaternary nitrogen atoms present, the antimicrobial quaternary ammonium compounds may be classified as monoalkyltrimethyl, monoalkyldimethylbenzyl, heteroaromatic, polysubstituted quaternary, bis-quaternary, or polymeric quaternary ammonium compounds.

A QAC is an ion, that is, a molecule that carries an electric charge. More specifically, a QAC is a cation, that is, an ion that possesses a positive charge. A nonionic molecule is an ion that possesses a neutral charge. An anion is an ion that possesses a negative charge. The charge of a molecule affects that molecule's intermolecular interactions. For example, a cation is attracted to an anion, and a cation repels another cation.

When QACs are applied directly to surfaces, their effect is not long-lasting due to leaching of the compound from the surface. Therefore, frequent applications may be needed to achieve prolonged antimicrobial effects.

The existing woven and nonwoven fabrics used in conjunction with sanitizing solutions to sanitize and disinfect surfaces reduce the concentration of sanitizer in the sanitizing solution rendering the sanitizing solution ineffective. Over a short period of time and under normal use, the existing fabrics reduce the concentration of sanitizer in the sanitizing solution to less than 200 parts per million. The surfaces of woven fabrics are treated with a surfactant to achieve the surface quality desired. A sufactant is a chemical additive that changes the surface attraction between two liquids, or between a liquid and a solid, by changing the surface energy of one or both components. Woven fabrics in common use today with sanitizing solutions are made with anionic surfactants. Nonwoven fabrics are constructed of loose strands of material that are bound together with binders. A binder is an adhesive, applied with a solvent or by melting a softenable plastic, to bond fibers together in a web or one web to another. Nonwoven fabrics in common use today with sanitizing solutions are made with anionic binders and surfactants.

The negative charge of the anionic binders and surfactants utilized in substrates today attracts and bonds the cationic QAC-based sanitizer to the fabric thereby reducing and neutralizing the concentration of sanitizer in the sanitizing solution. Moreover, woven fabrics comprise many interwoven strands of material, thereby creating a large irregular surface area that captures a large number of cationic QACs during use, thereby reducing the concentration of sanitizer in the sanitizing solution. Existing methods to solve this problem are to regularly replace the sanitizing solution or regularly replenish the concentration of sanitizer. However, these existing methods are not without limitations and disadvantages.

These existing methods are time consuming and expensive. Regularly monitoring and replacing or replenishing the sanitizing solution involves considerable employee time and the expense associated with replacing or replenishing the sanitizing solution. Additionally, during busy times in many restaurants, replacement or replenishment of the sanitizing solution is often forgotten, resulting in insufficient levels of microbial reduction.

Therefore, a need has arisen for a sanitizer release polymer composition that is capable of preventing today's fabrics from bonding to the sanitizer. Further, a need has arisen for a substrate that does not bond to or neutralize the sanitizer. The present invention provides such a composition and substrate.

SUMMARY OF THE INVENTION

In one aspect, the present invention is directed to an article for sanitizing a surface utilizing a sanitizing solution that includes a sanitizer at an effective concentration level. The article includes a substrate that absorbs and holds the sanitizing solution, and a composition covering at least a portion of the substrate. The substrate may be, for example, a woven, nonwoven, or knit fabric, a foam or sponge, or other structure suitable for absorbing and holding a sanitizing solution while wiping off a surface. The substrate has a structure that enables a user to wipe the surface with the substrate, thereby applying the sanitizing solution to the surface. The composition is operable to maintain the concentration level of the sanitizer at the effective level.

In another aspect, the present invention is directed to a sanitizing towel utilized to sanitize one of a plurality of areas in a restaurant utilizing a sanitizing solution that includes a sanitizer at an effective concentration level. The sanitizing towel includes a substrate that absorbs and holds the sanitizing solution, and enables a user to apply the sanitizing solution to the surface. The substrate may be selected from the group consisting of woven fabrics, nonwoven fabrics, knit fabrics, and foams. A sanitizer release polymer composition covers at least a portion of the substrate, and is operable to maintain the concentration level of the sanitizer at the effective level. Preferably, the sanitizer release polymer composition comprises at least one cationic surfactant which, in the preferred embodiment, is present in the sanitizer release polymer composition in an amount of about 1 to about 10 weight percent, based on a total weight of the sanitizer release polymer composition. In an alternative embodiment, the sanitizer release polymer composition comprises at least one nonionic surfactant.

In yet another aspect, the present invention is directed to a method of treating a substrate utilized with a sanitizing solution to maintain a sanitizer in the sanitizing solution at an effective concentration level. The method includes the steps of selecting a substrate, selecting a cationic (or nonionic) surfactant for applying to the substrate, and applying the surfactant to the substrate. The surfactant may be a component in a sanitizer release polymer composition in which the surfactant is present in an amount of about 0.1 to about 99 weight percent, based on a total weight of the sanitizer release polymer composition. The composition may be applied to the substrate by diluting the composition with water or an organic solvent, and applying the diluted composition by dip coating, spray coating, or foam coating.

BRIEF DESCRIPTION OF THE DRAWING

The invention will be better understood and its numerous objects and advantages will become more apparent to those skilled in the art by reference to the following drawing, in conjunction with the accompanying specification, in which.

DETAILED DESCRIPTION OF EMBODIMENTS

Figure 1:
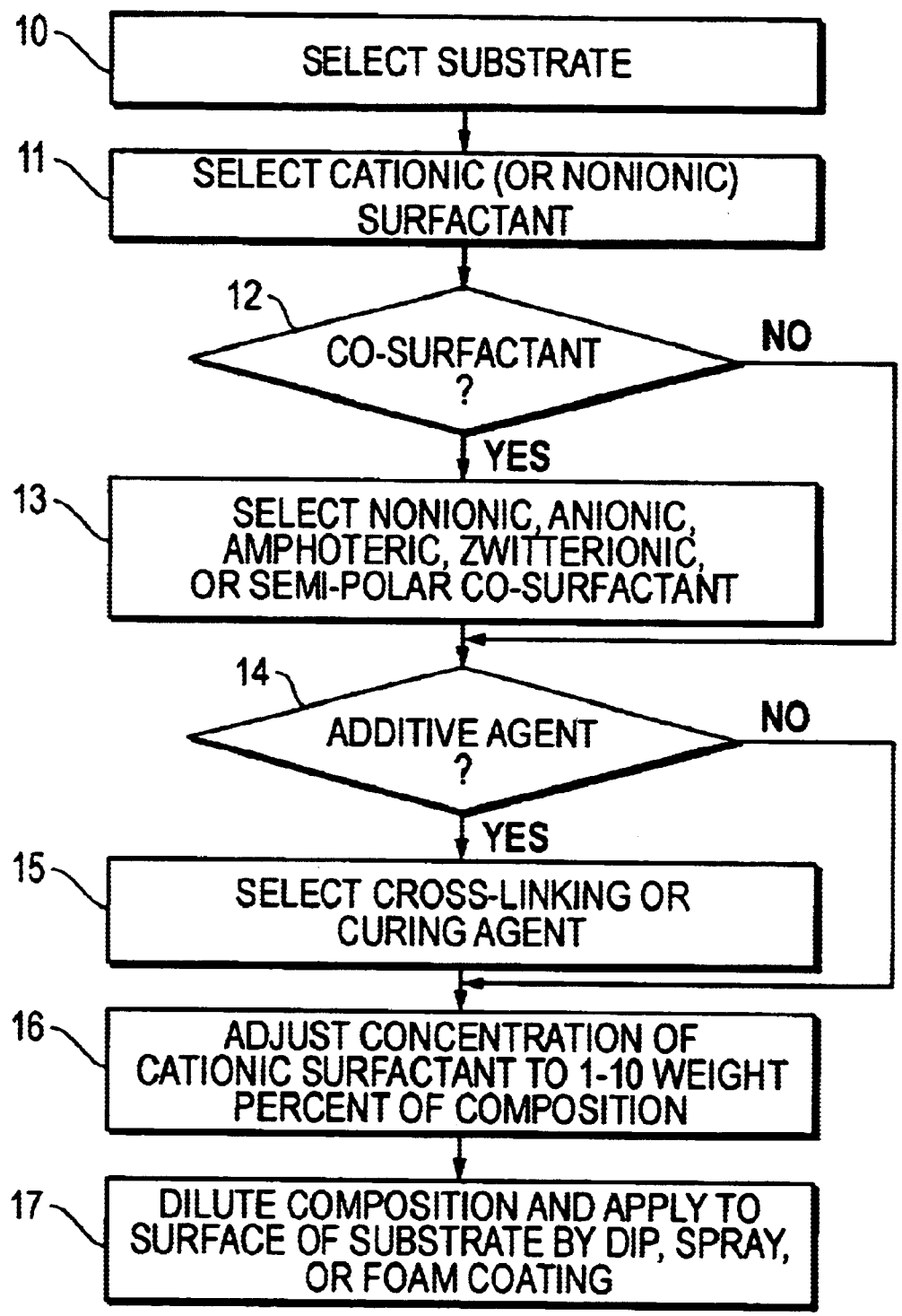
FIG. 1 is a flow chart outlining the steps of a process for manufacturing a treated substrate in accordance with the teachings of the present invention.

Preferred embodiments of the invention will now be described with reference to various examples of how the invention can best be made and used.

The present invention provides substrate treated with an enhanced sanitizer release polymer composition. The substrate may be any suitable material that can be treated with the enhanced sanitizer release polymer composition, and that will absorb sanitizing solution for wiping and sanitizing surfaces. For example, the substrate may be a woven, nonwoven, or knit fabric, a foam or sponge-like material, or the like. The enhanced sanitizer release polymer composition contains at least one cationic or nonionic surfactant. Optionally, the enhanced sanitizer release polymer composition may contain a co-surfactant. Optionally, the enhanced sanitizer release polymer composition may contain one or more additive agents that functionally and chemically improve the bonding of the cationic surfactant and optional co-surfactant(s) to a particular substrate. Optionally, the enhanced sanitizer release polymer composition may contain one or more fillers. In an alternative embodiment, the enhanced sanitizer release polymer composition contains only nonionic surfactants.

The purpose of any finish, such as a surfactant, is to improve the aesthetic, functional or processing properties of substrates. Surfactants are a class of materials broadly characterized as being made of molecules containing hydrophilic groups adequately separated from hydrophobic groups. The hydrophobic groups have an affinity for the fiber surface. The hydrophilic groups are attached predominantly to the aqueous medium. Existing substrates used in the field of sanitizers use anionic surfactants which have the negative effect of attracting the cationic QAC-based and cationic chlorine-based sanitizers thereby reducing the concentration of sanitizer in the sanitizing solution. The enhanced sanitizer release polymer composition of the present invention achieves its unexpectedly superior sanitizer release properties by preferably using a cationic surfactant that repels the cationic QAC-based and cationic chlorine-based sanitizers and prevents the sanitizer from bonding to the substrate. This enables the substrate to be used repeatedly with the sanitizing solution without significantly reducing the concentration of sanitizer in the sanitizing solution.

As noted, the enhanced sanitizer release polymer composition preferably contains at least one cationic surfactant, and may contain a co-surfactant. Suitable co-surfactants are selected from nonionic, anionic, amphoteric, zwitterionic, and semi-polar surfactants. A combination of cationic surfactants and co-surfactants may also be used. Preferably, the enhanced sanitizer release polymer compositions are prepared with either cationic surfactants or a combination of cationic and nonionic surfactants. For nonwoven fabrics, the composition may include cationic binders or a combination of cationic and nonionic binders.

Suitable cationic surfactants include, for example:

dieicosyldimethyl ammonium chloride;

didocosyldimethyl ammonium chloride;

dioctadecyldimethyl ammonium chloride;

dioctadecyldimethyl ammonium methosulphate;

ditetradecyldimethyl ammonium chloride and naturally occurring mixtures of above fatty groups, e.g. di(hydrogenated tallow)dimethyl ammonium chloride;

di(hydrogenated tallow)dimethyl ammonium methosulphate;

ditallow dimethyl ammonium chloride; and dioleyldimethyl ammonium chloride.

Cationic surfactants also include imidazolinium compounds, for example, 1-methyl-1-(tallowylamido-)ethyl-2-tallowyl4,5-dihydroimidazolinium methosulphate and 1-methyl-1-(palmitoylamido)ethyl-2-octadecyl 4,5-dihydro-imidazolinium methosulphate. Other useful imidazolinium materials are 2-heptadecyl-1-methyl-1(2-stearoylamido)-ethyl-imidazolinium methosulphate and 2-lauryl-lhydroxyethyl-1-oleyl-imidazolinium chloride.

Further examples of the cationic surfactant include:

dialkyl ($C_{12}$–$C_{22}$)dimethylammonium chloride;

alkyl(coconut)dimethylbenzylammonium chloride;

octadecylamine acetate salt;

tetradecylamine acetate salt;

tallow alkylpropylenediamine acetate salt;

octadecyltrimethylammonium chloride;

alkyl(tallow)trimethylammonium chloride;

dodecyltrimethylammonium chlorid;

alkyl(coconut)trimethylammonium chloride;

hexadecyltrimethylammonium chloride;

biphenyltrimethylammonium chloride, alkyl(tallow)-imidazoline quaternary salt;

tetradecylmethylbenzylammonium chloride;

octadecyidimethylbenzylammonium chloride;

dioleyidimethylammonium chloride;

polyoxyethylene dodecylmonomethylammonium chloride;

polyoxyethylene alkyl($C_{12}$–$C_{22}$)benzylammonium chloride;

polyoxyethylene laurylmonomethyl ammonium chloride;

1-hydroxyethyl-2-alkyl(tallow)-imidazoline quaternary salt; and a silicone cationic surfactant having a siloxane group as a hydrophobic group, a fluorine-containing cationic surfactant having a fluoroalkyl group as a hydrophobic group.

Anionic surfactants include, for example:

from $C_8$ to $C_{20}$ alkylbenzenesulfonates;

from $C_8$ to $C_{20}$ alkanesulfonates;

from $C_8$ to $C_{20}$ alkylsulfates;

from $C_8$ to $C_{20}$ alkylsulfosuccinates; and from $C_8$ to $C_{20}$ sulfated ethoxylated alkanols.

Nonionic surfactants include, for example, from $C_6$ to $C_{12}$ alkylphenol ethoxylates, from $C_8$ to $C_{20}$ alkanol alkoxylates, and block copolymers of ethylene oxide and propylene oxide. Optionally, the end groups of polyalkylene oxides can be blocked, whereby the free OH groups of the polyalkylene oxides can be etherified, esterified, acetalized and/or aminated. Another modification consists of reacting the free OH groups of the polyalkylene oxides with isocyanates. The nonionic surfactants also include $C_4$ to $C_{18}$ alkyl glucosides as well as the alkoxylated products obtainable therefrom by alkoxylation, particularly those obtainable by reaction of alkyl glucosides with ethylene oxide.

Amphoteric surfactants contain both acidic and basic hydrophilic groups. Amphoteric surfactants are preferably derivatives of secondary and tertiary amines, derivatives of quaternary ammonium, quaternary phosphonium or tertiary sulfonium compounds. The cationic atom in the quaternary compound can be part of a heterocyclic ring. The amphoteric surfactant preferably contains at least one aliphatic group, containing about 3 to about 18 carbon atoms.

At least one cationic surfactant is present in the enhanced sanitizer release polymer composition in an amount of from about 0.1 to about 99 weight percent, preferably from 0.5 to 50 weight percent, and more preferably from 1 to 10 weight percent, based on the total weight of the enhanced sanitizer release polymer composition. Preferable surfactants, such as the surfactants discussed above, can be obtained from Chicopee, Inc. of Dayton, New Jersey, a part of Polymer Group Inc. (PGI).

The composition of the additive agents, such as, for example, crosslinking or curing agents, that functionally and chemically improve the bonding of the cationic surfactant and optional co-surfactant to a particular substrate will depend on the composition and rheology of the substrate.

FIG. 1 is a flow chart outlining the steps of a process for manufacturing a treated substrate which may be utilized as, for example, a restaurant sanitizing towel. At step 10, a suitable cationic (or alternatively, a nonionic) surfactant is selected for use in the sanitizer release polymer composition.

At step 11, it is determined whether or not a co-surfactant is also to be utilized in the composition. If not, the process moves to step 13. However, if a co-surfactant is to be utilized, the process moves to step 12 where a suitable co-surfactant is selected from nonionic, anionic, amphoteric, zwitterionic, or semi-polar surfactants. At step 13, it is then determined whether or not an additive agent is also to be utilized in the composition. If not, the process moves to step 15. However, if an additive agent is to be utilized, the process moves to step 14 where an additive agent such as, for example, a cross-linking or curing agent is selected.

At step 15, the concentration of the cationic surfactant is preferably adjusted in the composition to a range of 1 to 10 weight percent, based on the total weight of the enhanced sanitizer release polymer composition. The process then moves to step 16 where the enhanced sanitizer release polymer composition is applied to the surface of the substrate. It should be understood by one skilled in the art that the bonding of the enhanced sanitizer release polymer composition to a substrate will depend on the composition and rheology of the substrate. The enhanced sanitizer release polymer composition of the present invention may be applied to the surface of the substrate by any suitable method. For example, the enhanced sanitizer release polymer composition may be diluted with an organic solvent or water, and the resulting solution applied to the surface of the substrate by dip coating, spray coating or foam coating.

It should be understood by one skilled in the art that the bonding of the enhanced sanitizer release polymer composition to a substrate will depend on the composition and rheology of the substrate. The enhanced sanitizer release polymer of the present invention can be applied to the surface of the substrate by any suitable method. For example, the enhanced sanitizer release polymer composition may be diluted with an organic solvent or water, and the resulting solution may be applied to the surface of the substrate to be treated by dip coating, spray coating, or foam coating.

Table 1 below summarizes test results obtained with a substrate treated with the enhanced sanitizer release polymer composition in accordance with the teachings of the present invention. The test results show the QAT concentration (ppm) of a sanitizing solution that was utilized with different substrates over a four-hour period. The results for each substrate are compared with the QAT concentration of a control solution that was not used during the test period.

TABLE 1

|  | Control | Invention | Generic 2 oz FST | Terry Cloth | Linen |
|---|---|---|---|---|---|
| After first Use | 203 | 203 | 177 | 180 | 174 |
| After 1 hour | 202 | 197 | 159 | 147 | 130 |
| After 2 hours | 202 | 203 | 133 | 119 | 88 |
| After 4 hours | 203 | 203 | 124 | 91 | 62 |

It can be readily seen that the inventive substrate and composition maintained the QAT concentration at the original level throughout the four-hour test period, matching the control solution which was not used. Traditional substrates such as the generic 2-oz Food Service Towel (FST), the Terry cloth, and the linen all substantially reduced the QAT concentration of the sanitizing solution during the test period.

It is thus believed that the composition of the present invention will be apparent from the foregoing description. Although the invention has been described with reference to certain exemplary arrangements, it is to be understood that the forms of the invention shown and described are to be treated as preferred embodiments. Various changes, substitutions and modifications can be realized without departing from the scope of the invention as defined in the following claims.

What is claimed is:

1. An article for sanitizing a surface utilizing a sanitizing solution that includes a sanitizer comprising positively charged ions at an effective concentration level, said article comprising:
   a substrate that absorbs and holds the sanitizing solution, said substrate having a structure that enables a user to wipe the surface with the substrate, thereby applying the sanitizing solution to the surface; and
   an adhesive binder that binds together the structure of the substrate, said binder including positively or neutrally charged ions that provide the substrate with a predominantly positive or neutral charge that prevents the substrate from neutralizing the positively charged ions in the sanitizer when the sanitizer is subsequently applied to the substrate, thereby maintaining the concentration level of the sanitizer at the effective level.

2. The article of claim 1 wherein the article is further treated with a cationic surfactant applied to the surface of the substrate.

3. The article of claim 1 wherein the binder includes the positively or neutrally charged ions in an amount of about 0.1 to about 99 weight percent, based on a total weight of the binder.

4. The article of claim 3 wherein the binder includes the positively or neutrally charged ions in an amount of about 0.5 to about 50 weight percent, based on a total weight of the binder.

5. The article of claim 4 wherein the binder includes the positively or neutrally charged ions in an amount of about 1 to about 10 weight percent, based on a total weight of the binder.

6. The article of claim 2 wherein the cationic surfactant is selected from the group consisting of:
   dieicosyldimethyl ammonium chloride;
   didocosyldimethyl ammonium chloride;
   dioctadecyldimethyl ammonium chloride;
   dioctadecyldimethyl ammonium methosulphate;
   ditetradecyldimethyl ammonium chloride and naturally occurring mixtures of fatty groups;
   di(hydrogenated tallow)dimethyl ammonium methosulphate;
   ditallow dimethyl ammonium chloride; and
   dioleyldimethyl ammonium chloride.

7. The article of claim 2 wherein the article is also treated with a co-surfactant selected from the group consisting of:
   a nonionic surfactant;
   an anionic surfactant;
   an amphoteric surfactant;
   a zwitterionic surfactant; and
   a semi-polar surfactant.

8. The article of claim 7 wherein the amphoteric surfactant is selected from the group consisting of:
   derivatives of secondary and tertiary amines;
   derivatives of quaternary ammonium;
   quaternary phosphonium; and
   tertiary sulfonium compounds.

9. The article of claim 2 wherein the cationic surfactant includes at least one additive agent that provides for improved bonding of the cationic surfactant to the substrate.

10. The article of claim 1 wherein the binder also includes at least one filler.

11. The article of claim 2 wherein the article is also treated with at least one nonionic co-surfactant selected from the group consisting of:
    $C_6$ to $C_{12}$ alkylphenol ethoxylates;
    $C_8$ to $C_{20}$ alkanol alkoxylates;
    block copolymers of ethylene oxide and propylene oxide;
    $C_4$ to $C_{18}$ alkyl glucosides; and
    alkoxylated products obtainable from $C_4$ to $C_{18}$ alkyl glucosides by alkoxylation.

12. The article of claim 1 wherein the article is further treated with a nonionic surfactant applied to the surface of the substrate.

13. The article of claim 12 wherein the nonionic surfactant is selected from the group consisting of:
    $C_8$ to $C_{12}$ alkylphenol ethoxylates;
    $C_8$ to $C_{20}$ alkanol alkoxylates;
    block copolymers of ethylene oxide and propylene oxide;
    $C_4$ to $C_{18}$ alkyl glucosides; and
    alkoxylated products obtainable from $C_4$ to $C_{18}$ alkyl glucosides by alkoxylation.

14. The article of claim 1 wherein the substrate is a nonwoven fabric comprising a multiplicity of strands of material that are bound together by the adhesive binder.

15. The article of claim 1 wherein the substrate is selected from the group consisting of woven fabrics, nonwoven fabrics, knit fabrics, and foams.

16. The article of claim 15 wherein the article is a sanitizing towel utilized to sanitize one of a plurality of areas in a restaurant.

17. A method of manufacturing a substrate, said substrate being utilized with a sanitizing solution that includes a sanitizer comprising positively charged ions, said method comprising the steps of:
    selecting an adhesive binder comprising predominantly positively or neutrally charged ions; and
    applying the binder to a plurality of loose strands of material to bind the strands together into a web-like structure forming the substrate;
    whereby, when the substrate is utilized with the sanitizing solution, the positively or neutrally charged ions in the binder prevent the substrate from neutralizing the positively charged ions in the sanitizer.

18. The method of claim 17 wherein the step of selecting a substrate includes selecting a substrate from the group consisting of woven fabrics, nonwoven fabrics, knit fabrics, and foams.

19. The method of claim 17 further comprising applying a cationic surfactant to the surface of the substrate, said cationic surfactant being selected from the group consisting of:
    dieicosyldimethyl ammonium chloride;
    didocosyldimethyl ammonium chloride;
    dioctadecyldimethyl ammonium chloride;
    dioctadecyldimethyl ammonium methosulphate;
    ditetradecyldimethyl ammonium chloride and naturally occurring mixtures of fatty groups;
    di(hydrogenated tallow)dimethyl ammonium methosulphate;

ditallow dimethyl ammonium chloride; and dioleyldimethyl ammonium chloride.

20. The method of claim 19 wherein the step of applying the cationic surfactant to the surface of the substrate includes the steps of:

mixing a composition in which the cationic surfactant is present in an amount of about 0.1 to about 99 weight percent, based on a total weight of the composition; and applying the composition to the substrate.

21. The method of claim 20 wherein the step of mixing a composition includes mixing a composition in which the cationic surfactant is present in an amount of about 1 to about 10 weight percent, based on a total weight of the composition.

22. The method of claim 20 wherein the step of applying the composition to the substrate includes the steps of:

diluting the composition with an organic solvent; and dip coating the substrate in the diluted composition.

23. The method of claim 20 wherein the step of applying the composition to the substrate includes the steps of:

diluting the composition with an organic solvent; and spray coating the substrate with the diluted composition.

24. The method of claim 20 wherein the step of applying the composition to the substrate includes the steps of:

diluting the composition with an organic solvent; and foam coating the substrate with the diluted composition.

25. The method of claim 20 wherein the step of applying the composition to the substrate includes the steps of:

diluting the composition with water; and dip coating the substrate in the diluted composition.

26. The method of claim 20 wherein the step of applying the composition to the substrate includes the steps of:

diluting the composition with water; and spray coating the substrate with the diluted composition.

27. The method of claim 20 wherein the step of applying the composition to the substrate includes the steps of:

diluting the composition with water; and foam coating the substrate with the diluted composition.

28. The method of claim 20 further comprising the steps of:

selecting a nonionic co-surfactant for use with the cationic surfactant in the composition; and mixing the nonionic co-surfactant with the cationic surfactant to form the composition.

29. The method of claim 20 further comprising the steps of:

selecting an additive agent for use with the cationic surtactant in the composition, said additive agent being operable to improve bonding of the cationic surfactant to the substrate; and mixing the additive agent with the cationic surfactant to form the composition.

30. A combination for sanitizing a surface, said combination comprising:

a liquid sanitizing solution that includes a sanitizer comprising positively charged ions at an effective concentration level;

a substrate that absorbs and holds the sanitizing solution, said substrate having a structure that enables a user to wipe the surface with the substrate, thereby applying the sanitizing solution to the surface; and an adhesive binder that binds together the structure of the substrate, said binder including positively or neutrally charged ions that provide the substrate with a predominantly positive or neutral charge that prevents the substrate from neutralizing the positively charged ions in the sanitizer when the sanitizer is subsequently applied to the substrate, thereby maintaining the concentration level of the sanitizer at the effective level.

31. The combination of claim 30 wherein the sanitizer in the sanitizing solution is a quaternary ammonium compound (QAC)-based sanitizer.

32. A combination for sanitizing a surface, said combination comprising:

a liquid sanitizing solution that includes a sanitizer comprising positively charged ions at an effective concentration level; and a cationic or nonionic substrate that absorbs and holds the sanitizing solution, said substrate having a structure that enables a user to wipe the surface with the substrate, thereby applying the sanitizing solution to the surface, said substrate having a cationic surfactant bonded to the surface of the substrate during manufacturing to provide the substrate with a predominantly positive or neutral charge, thereby preventing the substrate from neutralizing the positively charged ions in the sanitizer when the sanitizer is subsequently applied to the substrate.

33. A method of manufacturing an article for sanitizing surfaces, said article being utilized with a sanitizing solution that includes a sanitizer comprising positively charged ions, said method comprising the steps of:

selecting a substrate for the article having a structure suitable for absorbing and holding the sanitizing solution during use;

selecting a cationic surfactant comprising predominantly positively charged ions; and bonding the cationic surfactant to the surface of the substrate to provide the substrate with a predominantly positive or neutral charge;

whereby, when the article is subsequently utilized with the sanitizing solution, the positively or neutrally charged substrate prevents the article from neutralizing the positively charged ions in the sanitizer.

* * * * *